(12) United States Patent
Valent et al.

(10) Patent No.: US 11,806,115 B2
(45) Date of Patent: Nov. 7, 2023

(54) SYSTEMS AND METHODS FOR DYNAMIC SELECTION OF SENSORS FOR OBTAINING PHYSIOLOGICAL DATA FROM A PATIENT

(71) Applicant: GE Precision Healthcare LLC, Milwaukee, WI (US)

(72) Inventors: Thomas Valent, Burlington, WI (US); Mohammad Khair, Whitefish Bay, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 300 days.

(21) Appl. No.: 16/880,769

(22) Filed: May 21, 2020

(65) Prior Publication Data

US 2021/0361171 A1   Nov. 25, 2021

(51) Int. Cl.
*A61B 5/0205* (2006.01)
*A61B 5/00* (2006.01)
*A61B 5/0531* (2021.01)
*A61B 5/282* (2021.01)

(52) U.S. Cl.
CPC .......... *A61B 5/0205* (2013.01); *A61B 5/0006* (2013.01); *A61B 5/0024* (2013.01); *A61B 5/0531* (2013.01); *A61B 5/282* (2021.01); *A61B 5/6813* (2013.01); *A61B 5/746* (2013.01); *A61B 2503/045* (2013.01); *A61B 2562/02* (2013.01); *A61B 2562/046* (2013.01)

(58) Field of Classification Search
CPC ... A61B 5/0205; A61B 5/0006; A61B 5/0024; A61B 5/0531; A61B 5/6813; A61B 5/746; A61B 2503/045; A61B 2562/02; A61B 2562/046; A61B 5/30–5/308; A61B 5/318–367

See application file for complete search history.

(56) References Cited

U.S. PATENT DOCUMENTS

| | | | |
|---|---|---|---|
| 5,882,300 A | 3/1999 | Malinouskas et al. | |
| 7,245,956 B2 | 7/2007 | Matthews et al. | |
| 8,781,565 B2 * | 7/2014 | Vartak | A61B 5/25 600/513 |

(Continued)

OTHER PUBLICATIONS

PCT US2021/033317 filed May 20, 2021—International Search Report-Written Opinion dated Sep. 9, 2021; 16 pages.

*Primary Examiner* — Jonathan T Kuo
(74) *Attorney, Agent, or Firm* — McCoy Russell LLP

(57) ABSTRACT

Various methods and systems are provided for selecting sensors for acquiring physiological data of a patient. In one embodiment, a system comprises a plurality of sensors, a dynamic selection switch communicatively coupled to the plurality of sensors, a plurality of acquisition channels communicatively coupled to the dynamic selection switch, and a processor communicatively coupled to the dynamic selection switch and configured with executable instructions in non-transitory memory that when executed cause the processor to: select a subset of sensors; control the dynamic selection switch to connect the subset of sensors to the plurality of acquisition channels; and acquire, from the subset of sensors via the plurality of acquisition channels, physiological data of a patient. In this way, a subset of sensors in a plurality of sensors may be dynamically selected in real-time for acquiring physiological data of the patient.

21 Claims, 6 Drawing Sheets

(56) References Cited

U.S. PATENT DOCUMENTS

| | | | |
|---|---|---|---|
| 9,433,366 B2 | 9/2016 | Baker | |
| 9,629,572 B2 * | 4/2017 | Hill | A61B 5/4818 |
| 10,052,042 B2 * | 8/2018 | Jain | A61B 5/327 |
| 11,311,197 B2 * | 4/2022 | Yang | A61B 5/6805 |
| 2007/0049842 A1 * | 3/2007 | Hill | A61B 5/6804 |
| | | | 2/905 |
| 2011/0288605 A1 * | 11/2011 | Kaib | A61B 5/021 |
| | | | 607/5 |
| 2012/0215076 A1 * | 8/2012 | Yang | A61B 5/6885 |
| | | | 600/301 |
| 2013/0085367 A1 * | 4/2013 | Vartak | A61B 5/25 |
| | | | 600/393 |
| 2014/0327515 A1 * | 11/2014 | Luna | H04R 1/028 |
| | | | 340/4.42 |
| 2016/0287128 A1 * | 10/2016 | Jain | A61B 5/339 |
| 2018/0014784 A1 | 1/2018 | Heeger | |
| 2018/0360324 A1 | 12/2018 | Lorraine et al. | |
| 2020/0000411 A1 | 1/2020 | Franck | |
| 2020/0146573 A1 | 5/2020 | Rehfeldt | |
| 2020/0281496 A1 | 9/2020 | Obi | |

* cited by examiner

US 11,806,115 B2

SYSTEMS AND METHODS FOR DYNAMIC SELECTION OF SENSORS FOR OBTAINING PHYSIOLOGICAL DATA FROM A PATIENT

FIELD

Embodiments of the subject matter disclosed herein relate to an apparatus including a plurality of electrodes, the apparatus adapted to have direct, but non-adhering, contact with and measure an electrocardiogram signal of a patient.

BACKGROUND

An electrocardiogram (ECG) may provide a measurement of electric signals of the heart. Standard methods for measuring electric potential (e.g., bio-potentials) of a patient, and obtaining an ECG signal of the patient, may include securing electrodes directly to the skin of a patient. For example, a plurality of electrodes may be adhered to the patient's skin via an adhesive. An acquired ECG signal may be used to diagnose heart conditions of the patient, as well as determine a heart rate of the patient. The heart rate may be used for patient monitoring and diagnosis. When used in neonatal or infant care applications (often directly following delivery of the neonate/infant), the ECG signal and/or heart rate may be needed during resuscitation and/or monitoring of the patient for additional interventions.

BRIEF DESCRIPTION

In one embodiment, a system comprises a plurality of sensors distributed in an array and adapted to measure physiological data of a patient when in direct contact with a patient, a dynamic selection switch communicatively coupled to the plurality of sensors, a plurality of acquisition channels communicatively coupled to the dynamic selection switch, and a processor communicatively coupled to the dynamic selection switch and configured with executable instructions in non-transitory memory that when executed cause the processor to: select a subset of sensors from the plurality of sensors; control the dynamic selection switch to connect the subset of sensors to the plurality of acquisition channels; and acquire, from the subset of sensors via the plurality of acquisition channels, the physiological data of the patient. In this way, a subset of sensors in a plurality of sensors configured for measuring an electrocardiogram and/or heart rate of a patient such as a neonate or infant, for example by distributing the plurality of sensors throughout a fabric cover on which the patient is placed, may be dynamically selected in real-time for data acquisition.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
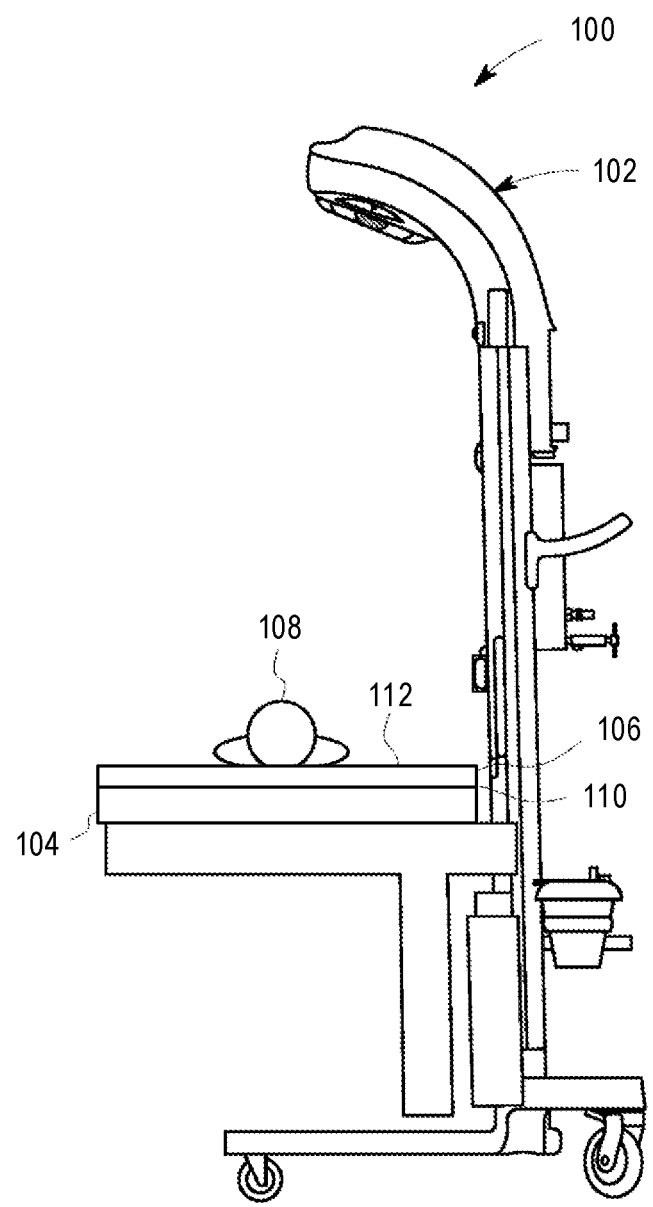
FIG. 1 shows an example of a neonate or infant care environment including a fabric cover with integrated sensors for direct contact with a patient.

The following description relates to various embodiments of an apparatus (e.g., fabric cover) including a plurality of electrodes for measuring an electrocardiogram signal of a patient in direct contact with at least a subset of the plurality of electrodes. For monitoring and care of a patient, such as a neonate or infant, an electrocardiogram (ECG) and/or heart rate signal of the patient may be acquired and displayed to a user (e.g., medical professional). As introduced above, standard electrodes for measuring an ECG signal of a patient may be adhered to the skin of the patient. However, such electrodes which are stuck to the patient's skin may cause damage to the more delicate skin of neonates or infants. Further, it may take a while for a medical professional to attach all the ECG leads (e.g., electrodes). However, the time to attach the ECG electrodes is often critical for administering essential and life-saving care to the neonate or infant. In one example, after birth, a neonate or infant may be placed in neonate or infant care environment (which may include a bassinet, warmer or incubator), on top of a platform or mattress. An apparatus, such as a fabric cover (which may be in the form of a blanket, bed sheet, or mattress cover in some embodiments) may include a plurality of electrodes (also referred to herein as sensors) attached or integrated therein. The fabric cover including an arrangement of electrodes may then be positioned in direct contact with the patient (e.g., placed on top of the mattress, with the patient lying directly on the fabric cover). When the patient is placed on the fabric cover with electrodes embedded therein, for example, a signal processing circuit, such as the signal processing circuit shown in FIG. 2, of or in electronic communication with electrodes of the fabric cover may automatically and immediately start acquiring bio-potential signals, also referred to herein generally as physiological data or physiological signals, of the patient. Though the electrodes of the fabric cover may be in direct contact with the skin of the patient, they may not be physically adhered (e.g., stuck) to the patient. As a result, as shown in FIG. 3, the patient may be able to move around across a surface of the electrodes and fabric cover, thereby changing which electrodes of the fabric cover are in direct contact with the skin of the patient. The electrodes may be arranged in an array and include a plurality of measurement electrodes (adapted to measure bio-potentials of the patient) and one or more driven electrodes (adapted to output a driven, common-mode output signal adapted to reduce noise of the measured bio-potential signals). The acquired bio-potential signals may then be used to determine an ECG signal and/or heart rate of the patient. As a result, a more accurate ECG signal with reduced noise may be obtained (continuously, in one example), even while a patient moves around on top of or against the fabric cover. This system may have minimal, passive contact with the patient, while still allowing for direct contact with the skin of the patient. As a result, an impact to the infant/neonate may be reduced. In order to dynamically switch which sensors or electrodes are being used for acquiring physiological data or bio-metric signals, as well as which sensor(s) or electrode(s) are being used for outputting a driven common-mode output signal, a system such as the system depicted in FIG. 4, may include a dynamic selection switch that selectively electrically connects a subset of sensors to acquisition channels and transmission channels. As depicted by FIG. 5, the dynamic selection switch is configured to electrically connect sensors determined to be in direct contact with the patient to acquisition channels and transmission channels, as well as electrically disconnect sensors not in direct contact with the patient, as the patient shifts position relative to the sensors. A method for monitoring a physiological state of a patient, as depicted by the method in FIG. 6, thus includes continually identifying which sensors are in direct contact with a patient and controlling the switch to connect selected sensors to acquisition channels and transmission channels, as well as dynamically updating which sensors are connected over time as the patient shifts position.

FIG. 1 shows an example of a neonate or infant care environment including a fabric cover with incorporated (e.g., integrated in one embodiment) sensors for direct contact with a patient. Specifically, FIG. 1 shows a neonatal or infant care environment 100. As shown in FIG. 1, environment 100 may include a neonate/infant radiant warmer 102, which may be referred to as a baby warmer that may include a mattress 104 for supporting a patient 108 (e.g., a neonate or infant). In alternate embodiments, environment 100 may be an incubator. In alternate embodiments, environment 100 may be a bassinet. The incubator and/or warmer and/or bassinet may be used in the neonatal intensive care unit (NICU) and/or right after labor and delivery of an infant.

An apparatus 110 having a sensor array is positioned between the mattress 104 and the patient 108. As used herein, the sensor array and sensors may also be referred to as an electrode array and electrodes, respectively. In the example shown in FIG. 1, the apparatus 110 is a fabric cover 106 that is positioned on/over the mattress 104 such that a top surface 112 of the fabric cover 106 is in direct contact with the patient 108. The fabric cover 106 includes a plurality of electrodes (e.g., sensors) integrated therein for measuring bio-potentials of the patient 108. As described further below, the plurality of electrodes may be arranged on the top surface 112 such that they may have direct contact with the skin of the patient 108. In one example, the fabric cover 106 may be a type of mattress pad or bed sheet. In another example, the fabric cover 106 may be a blanket.

As described further herein, the apparatus 110 may provide electrocardiogram (ECG) monitoring of patients such as neonates or infants. Apparatus 110 may consist of multiple sensors (e.g., electrodes) defining an array of sensors integrated with a remainder of the apparatus 110 (e.g., integrated with or sewn into a fabric of the fabric cover 106). The apparatus 110 may be transportable and reusable (e.g., washable). Further, the apparatus 110 may be inserted under the patient, such as a neonate or infant, and upon any surface, such as a blanket, mattress (as shown in FIG. 1), or mother's chest or abdomen. For example, as shown in and as described further below, the apparatus 110 may be integrated into a kangaroo care/wearable, skin-to-skin application, such as a sling, halter, wrap, nursing top, and the like. As described further below, apparatus 110 may include electronics for direct contact measurement of bio-potentials (e.g., heart rate), signal conditioning and processing, and/or wired or wireless communication with additional electronics, processors, or control units. Apparatus 110 may be configured for rapid measurement of ECG signals, even in the case where there is movement of the patient across the surface of the apparatus 110 (such that the patient changes which sensors/electrodes of the apparatus 110 are in direct contact with the patient). For example, apparatus 110 may enable measurement of ECG signals through motion artifacts associated with the patient's movements on the apparatus 110 (e.g., on the bed sheet or blanket).

Figure 2:
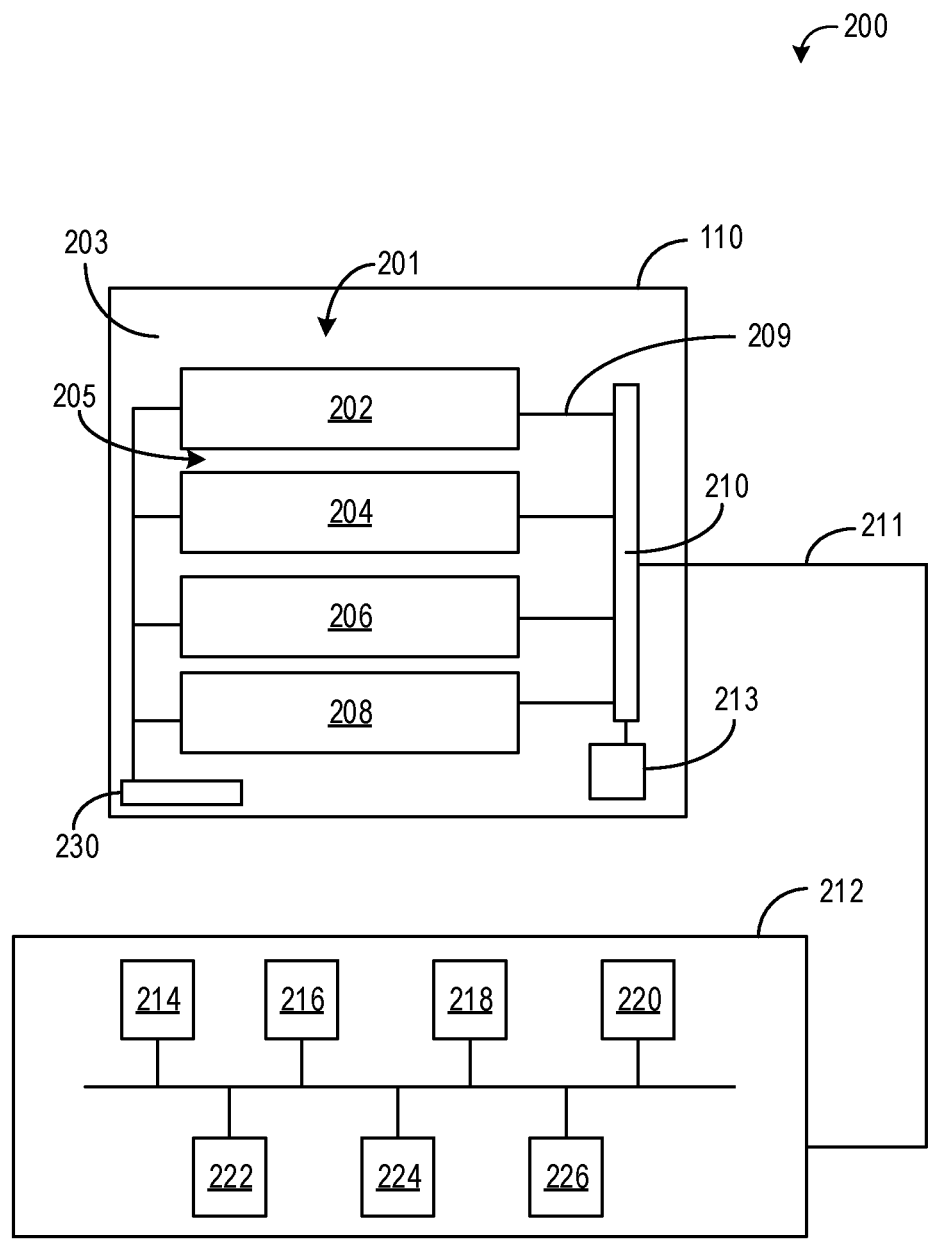
FIG. 2 shows an example block diagram of a system for measuring bio-potentials of a patient including an apparatus having a sensor array and a signal processing circuit.
Figure 3:
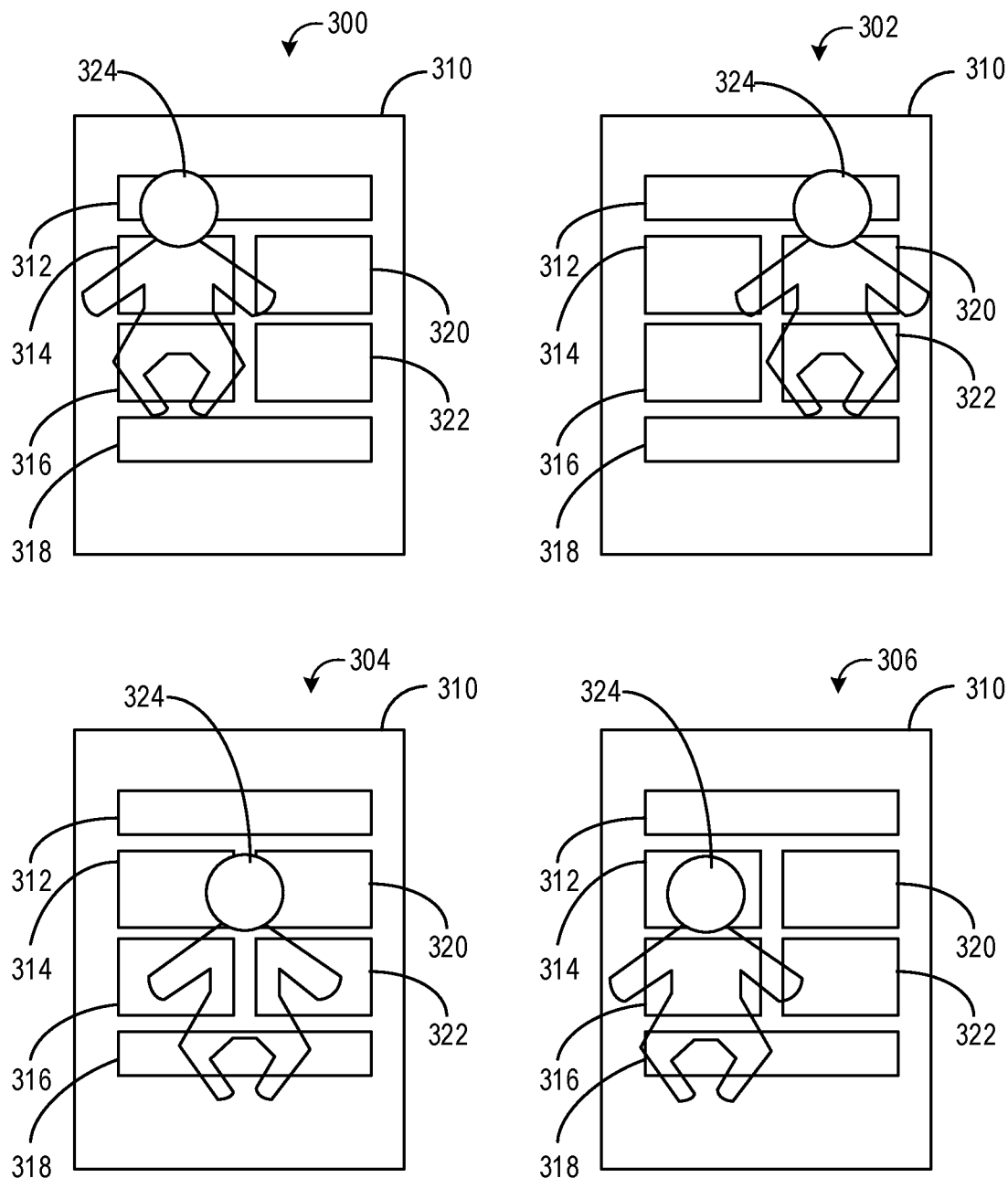
FIG. 3 shows a schematic of example positions of a patient on a fabric cover including a plurality of integrated sensors for measuring bio-potentials of the patient.

FIG. 2 shows an example block diagram of a system 200 for measuring bio-potentials of a patient (e.g., neonate or infant) including an apparatus 110 having a sensor array 201 and a signal processing circuit 212. The apparatus 110 may be a fabric cover (such as fabric cover 106 shown in FIG. 1, which may be a bed sheet, mattress cover, and/or blanket, in some embodiments, or such as fabric cover which may be a halter, sling, wrap, or the like). Thus, apparatus 110 may be or include a fabric base 203 with a plurality of individual sensors or electrodes (202, 204, 206, and 208) of the sensor array 201 integrated (e.g., embedded, sewn, incorporated, or affixed in some way) therein. As shown in FIG. 2, sensor array 201 includes four individual sensors 202, 204, 206, and 208, all spaced apart from one another (e.g., not touching or directly contacting one another) via a gap (e.g., distance) 205. However, in alternate embodiments, sensor array 201 may include more or less than four individual sensors (e.g., two, three, five, eight, ten, etc.). The individual sensors of sensor array 201 may be arranged in a pattern. Examples of different patterns of sensors of the sensor array for apparatus 110 are shown in FIG. 3. For all patterns, the individual sensors may be spaced apart from one another so that an amount of fabric of the fabric base 203 electrically insulates adjacent sensors from one another. In this way, electrical signals are not transferred between sensors.

In one embodiment, each of the sensors of sensor array 201 may be an electrode adapted to measure bio-potentials of the patient in direct contact with a surface of the sensors. The sensors (e.g., sensors 202, 204, 206, and 208) may also be referred to herein as ECG sensors since they are adapted to measure electrocardiogram (ECG) signals from the patient and determine a heart rate of the patient based on the measured signals. Sensor array 201 may include a plurality of measurement electrodes (e.g., which receive and measure ECG signals from the patient) and one or more dedicated, driven electrodes (e.g., which output a driven common mode output signal to the patient). In some examples, each of the measurement electrodes may be switched to be a driven electrode (e.g., switched from receiving bio-potential signals from the patient to delivering the common mode output signal to the patient). However, all of the dedicated, driven electrodes may remain driven electrodes and may not be switchable to measurement electrodes. In this way, the electrodes designated as dedicated, driven electrodes may only be used to output the driven common mode output signal and may not be used for measuring bio-potentials of the patient. As described further below, at any one time, one or multiple sensors may be selected to actively be the driven electrode and deliver the driven, common mode output signal. In one embodiment, first sensor 202, second sensor 204, and third sensor 206 may be measurement electrodes while fourth sensor 208 is a dedicated, driven electrode. In another embodiment, first sensor 202 and second sensor 204 may be measurement electrodes while third sensor 206 and fourth sensor 208 are dedicated, driven electrodes. In yet another embodiment, each of first sensor 202, second sensor 204, third sensor 206, and fourth sensor 208 may be measurement sensors adapted to be individually switched to functioning as a driven electrode. In yet another embodiment, each of first sensor 202, second sensor 204, third sensor 206, and fourth sensor 208 may be measurement sensors and where second sensor 204 and third sensor 206 are adapted to be both switched to functioning as a driven electrode. In this way, different combinations of measurement and driven electrodes included in sensor array 201 are possible.

Each individual sensor (202, 204, 206, and 208) is electrically coupled to an electronic connector 210 via a different electrical connection 209. In one embodiment, the electrical connections 209 may be conductive threads woven or imbedded within the fabric base 203. In this way, electrical signals may be passed back and forth between the individual sensors and the connector 210. For example, signals received by measurement electrodes from the patient may be transferred to the connector 210 via corresponding electrical connections 209 and the driven common mode output signal may be sent to the driven electrode from the connector 210 via corresponding electrical connection 209. A single connector 210 is shown in FIG. 2. However, in alternate embodiments, there may be multiple connectors (e.g., one for each individual sensor of sensor array 201).

The signal processing circuit 212 of system 200 is electrically coupled to the connector 210 (or connectors) via a wired or wireless connection 211. In one embodiment, all or select parts of the signal processing circuit 212 may be included within apparatus 110 and the processed signals may be transferred via a wireless connection to additional processing electronics or a remote data acquisition and/or display device. In this embodiment, the connector(s) 210 may be omitted. Alternatively or additionally, the apparatus 110 may include an integrated electronic layer 213 electrically coupled to (and/or included within) the connector 210 and adapted to perform measurements on electrical signals received from the plurality of sensors. For example, the integrated electronic layer may include one or more components of signal processing circuit 212 and/or a dynamic switching circuit (as described further below with reference to FIGS. 4 and 5). In another embodiment, as shown in FIG. 2, all the components of the signal processing circuit 212 may be located separate (e.g., remote) from the apparatus 110 and thus the connector(s) 210 and wired or wireless connection 211 may transfer electrical signals (acquired measurements and the driven signal) between the apparatus 110 and the signal processing circuit 212. In some embodiments, the connector 210 may include a wireless pod including a transmitter/receiver for transferring wireless signals between the apparatus 110 and the signal processing circuit 212. In another embodiment, apparatus 110 may include a separate wireless pod electrically coupled with the connector 210 or each individual sensor of sensor array 201. In still another embodiment, such as when the sensors and/or connector 210 are wirelessly connected to the signal processing circuit 212, the sensors may receive electrical power via a battery 230 incorporated into the apparatus 110 (e.g., incorporated into the fabric cover).

In one embodiment, signal processing circuit 212 may be processor based. In one embodiment, signal processing circuit 212 may include one or more input/output interface devices 214 for communication with, e.g., sensors 202, 204, 206, and 208 of sensor array 201, and/or one or more external processing circuits. One or more input/output interface devices 214 may include associated analog to digital and or digital to analog circuitry for facilitating bi-directional signal communication with sensor array 201. Signal processing circuit 212 may also include one or more central processing units (CPU) 216, one or more memory devices 218 (e.g. a random access memory (RAM) and/or cache memory, which may be volatile), one or more storage devices (e.g., non-volatile storage devices) 220, and one or more output devices 222. One or more memory devices 218 and/or one or more storage devices 220 may define a tangible computer readable storage medium of signal processing circuit 212. Signal processing circuit 212 may also include a power supply 224 which may be a battery-based power supply to facilitate mobile operation of signal processing circuit 212. One or more output devices 222, in one embodiment, may be provided, e.g., by one or more of a display with or without an associated touch screen and/or one or more audio output devices (e.g., a speaker). Devices 214, 216, 218, 220, 222, and 224, in one embodiment, are in communication via a system bus 226. Signal processing circuit 212 may output data via an output device 222 which may include a bus-connected output device, as shown in FIG. 2 and/or to an output device of apparatus 110 which is provided as an output device in communication with signal processing circuit 212 via input/output interface device 214.

Turning now to FIG. 3, a schematic is shown of example positions of a patient 324 on a fabric cover 310. Fabric cover 310 may be similar to apparatus 110 and/or fabric cover 106 discussed above with reference to FIGS. 1 and 2. As discussed above, the fabric cover 310 includes a plurality of integrated ECG sensors 312, 314, 316, 318, 320, and 322 which may be referred to herein as electrodes or electrode pads. Each of the ECG sensors are spaced apart from one another such that they are electrically insulated from one another (and thus cannot pass signals between one another, thereby reducing signal interference between ECG sensors) via the intervening fabric of the fabric cover 310. FIG. 3 shows an example arrangement of ECG sensors on a surface of the fabric cover 310 which is not meant to be limiting and other arrangements of ECG sensors are possible. As shown in the example of FIG. 3, the ECG sensors include a topmost ECG sensor 312, a top-left ECG sensor 314, a bottom-left ECG sensor 316, a bottommost ECG sensor 318, a bottom-right ECG sensor 322, and a top-right ECG sensor 320. The patient 324 may be smaller than the fabric cover 310 and thus may move around on top of and across the surface of the fabric cover 310. As such, at different points in time, the skin of the patient may be in contact with different ECG sensors of fabric cover 310. Thus, the dynamic switching circuit of the signal processing circuit included in or electrically coupled with the fabric cover 310 (such as the dynamic switching circuit described further herein with regard to FIGS. 4 and 5) may switch, in real-time (e.g., dynamically), which ECG sensors are selected as the measurement electrodes and driven electrode for producing the patient's ECG signal and determining the patient's heart rate, based on the patient's position on the fabric cover 310 (as determined according to the methods described herein with reference to FIG. 3 and FIG. 5).

Specifically, FIG. 3 shows a first view 300 of the patient (e.g., neonate or infant) 324 in a first position on the fabric cover 310 (e.g., top-left corner). In this first position, the patient 324 is in contact with the topmost ECG sensor 312, the top-left ECG sensor 314, and the bottom-left ECG sensor 316. While a small portion of the patient's arm may be contacting top-right sensor 320, there may not be enough skin-to-electrode contact to produce a strong enough skin impedance and measurement signal. Thus, the dynamic switching circuit of the fabric cover 310 may select ECG sensors 312, 314, and 316 as the contacting sensors (e.g., the ECG sensors having direct, face-sharing contact with a portion of the skin of the patient 324). One of the contacting ECG sensors 312, 314, and 316 may be selected to be the driven electrode (sensor) while the remaining two are selected as the measurement electrodes. Signals from the remaining ECG sensors (318, 320, 322), which are determined to be non-contacting ECG sensors, may be discarded (or not acquired) and not used to determine the ECG signal and heart rate of the patient. In one embodiment, ECG sensors 316 and 322 may be dedicated, driven electrodes. Thus, the dynamic switching circuit may automatically select bottom-left ECG sensor 316 to deliver the driven common mode output signal. In alternate embodiments, a different one or more of the ECG sensors of fabric cover 310 may be dedicated, driven electrodes. In yet another embodiment, all of the ECG sensors of fabric cover 310 may be measurement electrodes (e.g., none are dedicated to being driven only) adapted to switch between being measurement and driven electrodes (as determined and selected by the dynamic switching circuit). However, by including some dedicated driven electrodes and some switchable measurement electrodes, an electrode surface area is provided that is always available for common mode noise reduction if all of the measurement electrodes can be used to capture the ECG signal (e.g., because the measurement electrodes have good patient contact), which may improve signal processing outcomes to mitigate motion and noise artifacts using adaptive filtering by the CPU. Further, more ECG channels may improve the adaptive filtering outcomes, while using the measurement electrodes for providing the driven output reduces the number of channels available for signal processing post digitization, and thus it may be desirable to provide the dedicated, driven electrodes so that all possible channels may be available for the ECG signal acquisition.

FIG. 3 also shows a second view 302 of the patient 324 in a second position on the fabric cover 310 (e.g., top-right corner). In one example, the patient 324 may have moved from the first position (in first view 300) to the second position (in second view 302), thereby changing which of the ECG sensors the patient 324 is in direct, physical contact with (and thus changing the contact points of fabric cover 310). In this second position, the patient 324 is in contact with the topmost ECG sensor 312, top-right ECG sensor 320, and bottom-right ECG sensor 322. Thus, patient 324 is no longer contacting ECG sensors 314 and 316 and is newly contacting ECG sensors 320 and 322. Thus, in one example, the dynamic switching circuit may switch the driven electrode to be the bottom-right ECG sensor 322 (from the bottom-left ECG sensor 316 in first view 300), in response to the patient moving positions on the fabric cover 310 and changing which ECG sensors are contacting sensors. Further, the dynamic switching circuit may continue to use the topmost ECG sensors 312 as one measurement electrode and switch to using the top-right ECG sensor 320 (instead of the bottom-right ECG sensor 316, as used in first view 300) as a second measurement electrode.

In a third view 304 of FIG. 3, the patient 324 is in a third position on the fabric cover 310 (e.g., central-bottom region). In one example, the patient 324 may have moved from the second position (in second view 302) to the third position (in third view 304), thereby changing which of the ECG sensors the patient 324 is in direct, physical contact with (and thus changing the contact points of fabric cover 310). In this third position, the patient 324 is in contact with the top-left ECG sensor 314, the bottom-left ECG sensor 316, the bottommost ECG sensor 318, the bottom-right ECG sensor 322, and the top-right ECG sensor 320. Thus, patient 324 is no longer contacting the topmost ECG sensor 312, remains in contact with ECG sensors 320 and 322, and is newly contacting ECG sensors 314, 316, and 318 (as compared to second view 302). Thus, in one example, the dynamic switching circuit may maintain the driven electrode as the bottom-right ECG sensor 322 and not switch the driven electrode to a different ECG sensor. Further, the dynamic switching circuit may continue to use the top-right ECG sensor 320 as one measurement electrode and switch to using the top-left ECG sensor 314 and bottommost ECG sensor 318 as additional measurement electrodes. In the case where the bottom-left ECG sensor 316 is a dedicated, driven electrode, it may be used to apply the driven common mode output signal, in addition to the bottom-right ECG sensor 322 that is currently selected as the driven electrode.

In a fourth view 306 of FIG. 3, the patient 324 is in a fourth position on the fabric cover 310 (e.g., bottom-left). In one example, the patient 324 may have moved from the third position (in third view 304) to the fourth position (in fourth view 306), thereby changing which of the ECG sensors the patient 324 is in direct, physical contact with (and thus changing the contact points of fabric cover 310). In this fourth position, the patient 324 is in contact with the top-left ECG sensor 314, the bottom-left ECG sensor 316, and the bottommost ECG sensor 318. Thus, patient 324 is no longer contacting the top-right ECG sensor 320 and bottom-right ECG sensor 322 (e.g., even though a small portion of patient 324 is shown contacting sensor 322, not enough of the patient's skin is in contact with sensor 322, so the measured skin impedance of this sensor is below the threshold level) and remains in contact with ECG sensors 314, 316, and 318 (as compared to third view 304). Thus, in one example, the dynamic switching circuit may switch the driven electrode to be the bottom-left ECG sensor 316 (from the bottom-right ECG sensor 322). Further, the dynamic switching circuit may continue to use the top-left ECG sensor 314 and bottommost ECG sensor 318 as measurement electrodes.

In all of the views of FIG. 3, at least two contacting ECG sensors are selected as measurement electrodes and a different, one contacting ECG sensor is selected as the driven electrode. As such, the patient's ECG signal may be obtained with reduced noise (e.g., reduced noise from motion of the patient) from the acquired signals. As shown in the example of FIG. 3, the ECG sensors used as measurement electrodes and the driven electrode may be selected based on which sensors are determined to be directly contacting the skin of the patient and dynamically switched as the patient moves across the fabric cover, into different contacting positions, at least under some conditions. For example, the dedicated driven electrodes are fixed per the connection to the signal processing circuit 212 via wired or wireless connection 211. The dedicated driven electrodes are always enabled and driven. If using the impedance measurement it is sensed that the driven electrodes are not in contact with the patient, the system may then select which measurement electrodes are to be used for driving the output signal. Which sensors are selected and used as the driven electrode and measurement (e.g., input)

electrodes may be switched at any time during operation of the fabric cover (e.g., while the patient is on and/or in contact with the fabric cover). For example, switching of measurement and driven electrodes may be performed prior to the initial acquisition of the ECG signal (from the measurement electrodes). In another embodiment, switching of the measurement and driven electrodes may occur during ECG acquisition (e.g., while measurement signals are being acquired from the measurement electrodes), in response to determining the contacting ECG sensors have changed (e.g., the ECG sensors currently being used for determining the ECG signal are no longer in contact with the patient and need to be switched to other sensors that are in contact with the patient). A dynamic selection system for automatically connecting different configurations of sensors to acquisition channels for acquiring physiological data or measurement signals and transmission channels for transmitting or driving a driven signal is described further herein with regard to FIG. 4.

As shown in FIG. 3, multiple contacts between the patient and ECG sensor pads are made instantaneously upon application of the patient (e.g., infant/neonate) to a surface of the fabric cover. While the multiple contacts are direct contact points between the skin of the patient and the ECG sensor pads, none of the ECG sensor pads are stuck or mechanically adhered to the patient's skin (e.g., via an adhesive), thereby reducing damage and irritation to the infant/neonate's delicate skin. As also seen in the different views of FIG. 3, the patient is free to move over the surface of the fabric cover and sensor array. As such, the position of the patient on the sensor array may change, and thus which electrodes are in contact with the patient's skin may also change during operation/data collection. As discussed above and further below, the measurement and driven electrodes of the sensory array may be selected and switched according to this movement and change in the contacting sensors.

Figure 4:
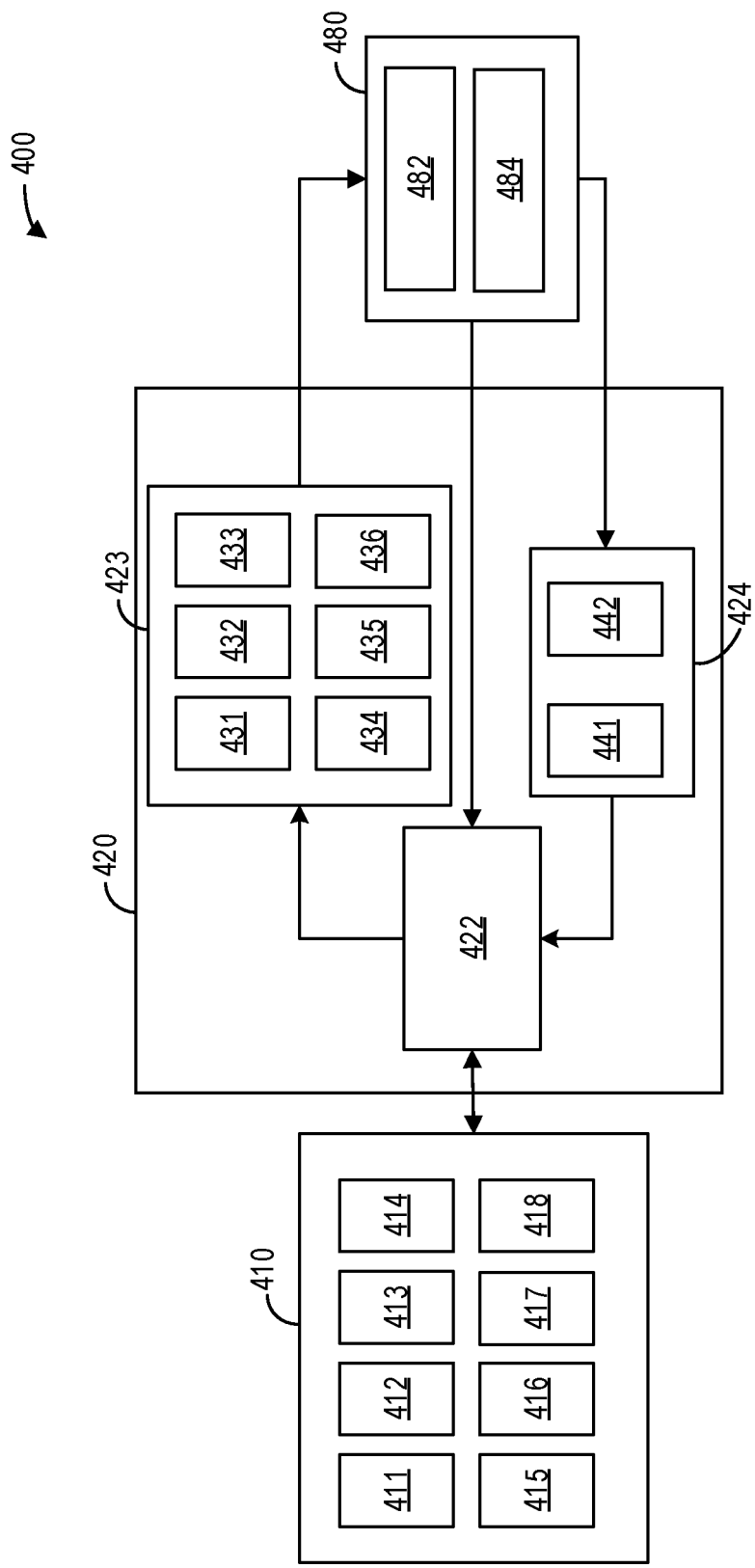
FIG. 4 shows a block diagram of an example system for dynamically switching sensors in an array of sensors between acquisition and transmission channels according to an embodiment.
Figure 5:
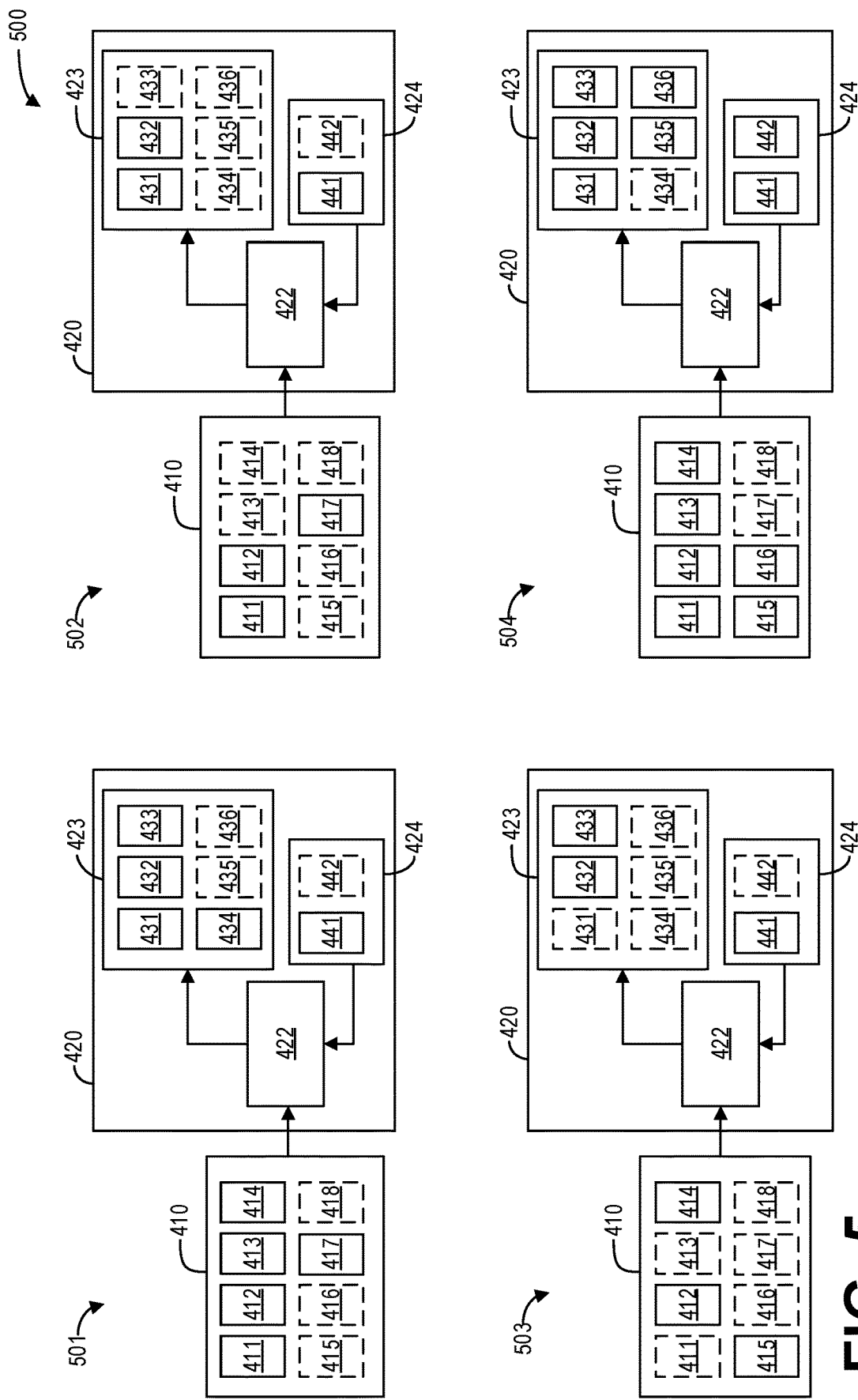
FIG. 5 shows a block diagram illustrating the system of FIG. 4 in various states corresponding to different positions of a patient according to an embodiment.

FIG. 4 shows an example block diagram illustrating an example dynamic selection system 400 for monitoring a patient. The dynamic selection system 400 comprises a plurality of sensors 410 arranged in an array and a monitoring system 420. The plurality of sensors 410 may comprise the sensor array 201, for example. The monitoring system 420 comprise a dynamic switching circuit or a dynamic switching apparatus configured to dynamically switch connect sensors of the plurality of sensors 410 to acquisition channels 423 and/or transmission channels 424 of the monitoring system 420. Physiological signals acquired via the plurality of sensors 410 are transmitted to a computing device 480 via the monitoring system 420, as depicted. The computing device 480 comprises a processor 482 and a non-transitory memory 484, as depicted. The computing device 480 may comprise the signal processing circuit 212, in some examples, or alternatively the computing device 480 may be integrated into the monitoring system 420. The plurality of sensors 410 may be integrated into a fabric cover as described hereinabove with regard to FIGS. 2 and 3. Furthermore, the monitoring system 420 may also be integrated into the fabric cover along with the plurality of sensors, for example, though in some examples the monitoring system 420 may be provided external to the fabric cover.

As depicted, the plurality of sensors 410 comprises a number of sensors including a first sensor 411, a second sensor 412, a third sensor 413, a fourth sensor 414, a fifth sensor 415, a sixth sensor 416, a seventh sensor 417, and an eighth sensor 418. The particular number of sensors and type of sensors may differ with the given sensor array, the clinical application for the plurality of sensors, and/or the specific device to which the sensors are connected. For example, the plurality of sensors 410 is depicted as including eight sensors, though it should be appreciated that the plurality of sensors 410 may include more than eight sensors or fewer than eight sensors depending on the design of the sensors (e.g., depending on the shape of each sensor) and/or the physical distribution of sensors relative to each other. With regard to the systems described hereinabove with regard to FIGS. 1-3, the plurality of sensors 410 may comprise ECG sensors or leads embedded within or integrated into a fabric cover or blanket. In another example, the plurality of sensors 410 may comprise EEG sensors for measuring brainwave activity. The plurality of sensors 410 are configured to measure physiological or biometric data of the patient and transmit the acquired data to the monitoring system 420. Furthermore, at least one sensor of the plurality of sensors 410 may be configured as a driven sensor to receive transmissions from the monitoring system 420, such as a driven common-mode output signal, to apply to the patient. In some examples, as mentioned hereinabove, all sensors of the plurality of sensors 410 may be configured for use as acquisition sensors and/or driven sensors. However, in other examples, only a subset of the plurality of sensors 410 may be configured for use as dedicated driven sensors.

The monitoring system 420 comprises a dynamic selection switch 422, a plurality of acquisition channels 423, and a plurality of transmission channels 424. The dynamic selection switch 422 is communicatively coupled to each sensor of the plurality of sensors 410 as well as the plurality of acquisition channels 423 and the plurality of transmission channels 424, as depicted. The dynamic selection switch 422 is configured to dynamically connect sensors of the plurality of sensors 410 to acquisition channels of the plurality of acquisition channels 423 and/or the plurality of transmission channels 424.

The plurality of acquisition channels 423 comprises a number of acquisition channels, including but not limited to a first acquisition channel 431, a second acquisition channel 432, a third acquisition channel 433, a fourth acquisition channel 434, a fifth acquisition channel 435, and a sixth acquisition channel 436. Although six acquisition channels are depicted in FIG. 4, it should be appreciated that the number of acquisition channels is illustrative and non-limiting, and that the plurality of acquisition channels may comprise more than six acquisition channels or fewer than six acquisition channels depending on the type of physiological monitoring. The number of acquisition channels may comprise a number of acquisition channels necessary for acquiring physiological data for monitoring a patient. The plurality of acquisition channels 423 transmit acquired signals from sensors of the plurality of sensors 410 to the computing device 480 are transferred through the selection switch device to the acquisition channels and transmission channels. The plurality of acquisition channels 423 are therefore used to collect and aggregate data from the plurality of sensors 410.

Similarly, the plurality of transmission channels 424 as depicted comprises a first transmission channel 441 and a second transmission channel 442. It should be appreciated that in some examples, the plurality of transmission channels 424 may comprise a single transmission channel, two transmission channels as depicted, or more than two transmission channels. The transmission channels are configured to transmit driving signals from the computing device 480 to the plurality of sensors 410. For example, with regard to the systems described hereinabove with regard to FIGS. 1-3, one or more transmission channels of the plurality of transmission channels 424 may transmit a driven right leg signal to a driven sensor of the plurality of sensors 410 for reducing common-mode interference during ECG data collection.

The dynamic selection switch 422 controls the connection of the plurality of sensors 410 and which channels of the acquisition channels 423 and transmission channels 424. In this way, the dynamic selection switch 422 controls which sensors of the plurality of sensors 410 are used for data acquisition, by connecting said sensors to the acquisition channels 423, as well as which sensors of the plurality of sensors 410 are used for transmitting driven signals to the patient, by connecting said sensors to the transmission channels 424. The dynamic selection switch 422 thus comprises an apparatus for dynamically connecting sensors to channels based on operating conditions. To that end, in some examples, the dynamic selection switch 422 may comprise a MOSFET-based switch. The dynamic selection switch 422 may be communicatively coupled to the computing device 480 and may receive control signals from the computing device 480 that indicate which sensors should be connected to which channels. For example, the computing device 480 may evaluate signals from each sensor of the plurality of sensors 410 to identify which sensors are in direct contact with a patient and are therefore suitable for data acquisition and/or transmission. The computing device 480 may then control the dynamic selection switch 422, via a control signal transmitted to the dynamic selection switch 422, to connect particular sensors of the plurality of sensors 410 to particular acquisition channels and/or particular transmission channels. An example method for controlling the dynamic selection switch 422 is described further herein with regard to FIG. 6.

For example, the computing device 480 may select a subset of sensors from the plurality of sensors 410 based on their impedance and relative positions. Should the patient shift position on the cover or blanket, then the dynamic selection switch 422 may automatically adjust which sensors are used for data collection and signal driving. In this way, the contacts used to collect biometric or physiological data and drive the driven signal can be reconfigured in real-time to ensure they capture an ECG signal with adequate fidelity.

To illustrate how the dynamic selection switch 422 may dynamically connect sensors of the plurality of sensors 410 to acquisition channels 423 and transmission channels 424, FIG. 5 shows a plurality of example configurations 500 of the dynamic selection system 400 for different scenarios. The example configurations 500 include a first configuration 501, a second configuration 502, a third configuration 503, and a fourth configuration 504. The plurality of example configurations 500 may occur over time while monitoring a patient, and in this way illustrate how the dynamic selection switch 422 may dynamically connect the sensors 410 to the channels 423 and 424 over time while monitoring the patient.

In the first configuration 501, the first sensor 411, the second sensor 412, the third sensor 413, and the fourth sensor 414 are selected for acquiring physiological data, while the seventh sensor 417 is selected for driving a driven signal. Thus, the dynamic selection switch 422 connects the first sensor 411 to the first acquisition channel 431, the second sensor 412 to the second acquisition channel 432, the third sensor 413 to the third acquisition channel 433, and the fourth sensor 414 to the fourth acquisition channel 434. Physiological data may thus be measured by the first sensor 411, the second sensor 412, the third sensor 413, and the fourth sensor 414 and acquired by the computing device 480 via the first acquisition channel 431, the second acquisition channel 432, the third acquisition channel 433, and the fourth acquisition channel 434, respectively. Further, the dynamic selection switch 422 connects the seventh sensor 417 to the first transmission channel 441, such that a driven common-mode output signal may be transmitted, via the transmission channel 441, to the seventh sensor 417. The seventh sensor 417 may thus apply the driven common-mode output signal to the patient to reduce common-mode interference.

If the operating conditions of the plurality of sensors 410 change, and in particular if the operating conditions of at least one sensor of the selected sensors 411, 412, 413, 414, and 417 change due to the patient shifting positions relative to the plurality of sensors 410, then the dynamic selection switch 422 may switch the sensors and acquisition channels to other configurations, including but not limited to the example configurations 502, 503, and 504.

For example, the patient may move such that only the first sensor 411, the second sensor 412, and the seventh sensor 417 are in direct contact with the patient. As depicted by the example configuration 502, the dynamic selection switch 422 may thus connect the first sensor 411 to the first acquisition channel 431, the second sensor 412 to the second acquisition channel 432, and the seventh sensor 417 to the first transmission channel 441. If the configuration is proceeding directly from the configuration 501 to the configuration 502, the dynamic selection switch 422 may disconnect the third sensor 413 and the fourth sensor 414 from the respective acquisition channels 433 and 434. Alternatively, depending on the physical distances between the sensors 411, 412, and 417, the dynamic selection switch 422 may connect the first sensor 411 and the seventh sensor 417 to the acquisition channels 431 and 432, for example, and the second sensor 412 to the first transmission channel 441 to obtain physiological data with relatively improved signal fidelity. Further, it should be appreciated that two sensors are connected to acquisition channels in the configuration 502, while four sensors are connected to acquisition channels in the configuration 501. That is, in some examples, while four sensors may be preferable for acquiring physiological data from a patient, the dynamic selection switch 422 may connect fewer than four sensors to acquisition channels if there are not enough sensors in direct contact with the patient to connect four sensors to acquisition channels. In this way, the dynamic selection system 400 described hereinabove may dynamically switch the number of sensors being used for data collection over time while monitoring a patient.

In the third example configuration 503, the sensors 412, 414, and 415 are in direct contact with the patient. The dynamic selection switch 422 may therefore connect two of the sensors, such as the second sensor 412 and the fourth sensor 414, to acquisition channels such as the second acquisition channel 432 and the third acquisition channel 433. The dynamic selection switch 422 may further connect one of the sensors, such as the fifth sensor 415, to the first transmission channel 441 for transmitting a driven signal to the fifth sensor 415. It should be appreciated that more sensors may be in direct contact with the patient but not connected to acquisition channels 423 or transmission channels 424 by the dynamic selection switch 422. The particular sensors selected for connection to the acquisition channels 423 and transmission channels 424 may be selected based on the relative position of the sensors, and in particular may be selected based on relative distance as well as relative position to obtain the best signal-to-noise ratio, as an illustrative example, for the acquired physiological data. For example, the sensor 416 may also be in direct contact with the patient, but may not be connected to an acquisition channel 423 or a transmission channel 424 as the position of the sensor 416 may not provide adequate noise performance when paired with another sensor for data acquisition and similarly may not be as optimal as a driven sensor relative to the selected pair of sensors for data acquisition. Should the operating conditions of the sensor array 410 change, then the dynamic selection switch 422 can switch the sensors and acquisition channels to other configurations, for example such as the configurations shown in views 501, 503, or 504, or other configurations not depicted.

In the fourth configuration 504, the sensors 411, 412, 413, 414, 415, and 416 are in direct contact with the patient. As there are six sensors in direct contact with the patient, the system may connect one sensor to the transmission channel 441 for driving a common-mode output signal to the patient, and may select one or two pairs of sensors from the remaining sensors in direct contact with the patient for connecting to the acquisition channels.

However, as another example, the dynamic selection switch 422 may connect the first sensor 411 to the acquisitions channels 431, 432, and 433, the fourth sensor 414 to the acquisition channel 435, and the fifth sensor 415 to the acquisition channel 436. It should thus be appreciated that a sensor such as the first sensor 411 may be connected to a plurality of acquisition channels 423 rather than a single acquisition channel. For example, the signal from the sensor 411 may be desirable to use as a reference for other sensor connections and as such may be connected to multiple acquisition channels 423. Additionally, the dynamic selection switch 422 may connect the third sensor 413 to the first transmission channel 441 for driving or transmitting a noise reduction signal to the third sensor 413, and the sixth sensor 416 to the second transmission channel 442 for driving or transmitting a respiratory signal modulation signal to the sixth sensor 416. The respiratory signal modulation signal comprises a signal that modulates the physiological signals acquired from the patient such that respiration signals may be extracted from the physiological signals. For example, ECG signals acquired via sensors connected to the acquisition channels 423 may be modulated by applying the respiratory signal modulation signal to the patient, such that respiratory signals may be extracted from the ECG signals more easily and with improved noise characteristics. Thus, in some examples, provided the transmission signal for noise reduction is different enough from the respiratory signal modulation signal, both transmission channels 441 and 442 may be connected via the dynamic selection switch 422 to the same third sensor 413 such that both signals are transmitted to the third sensor 413. In this way, the sixth sensor 416 may be available for use by the acquisition channels 423 or for connection to additional transmission channels not shown. Further, it should be noted that in the depicted example configuration 504, as described above, the dynamic selection switch 422 does not connect the second sensor 412 to the acquisition channels 423 or the transmission channels 424 despite being in direct contact with the patient.

Thus, the dynamic selection system 400 automatically and dynamically connects sensors in direct contact with the patient to acquisition channels and transmission channels in real-time while monitoring a patient. The dynamic selection switch 422 is controlled by a processor 482, for example, to electrically couple selected sensors to selected acquisition and/or transmission channels. The dynamic selection switch 422 further may electrically disconnect sensors from acquisition and/or transmission channels. For example, the number of acquisition channels 423 and the number of transmission channels 424 may be less than the number of sensors 410, and so only a subset of sensors 410 may be connected to acquisition or transmission channels at a given time. Further, in some examples, the dynamic selection system 400 allows for automatic switching between different lead configurations, such as between three-lead and five-lead configurations or even between three-lead and seven-lead configurations, while monitoring a patient, depending on the number of sensors in direct contact with the patient as well as the relative position of the sensors in direct contact with the patient. Further still, a sensor may be connected to two or more acquisition channels in some examples, such that signals from the sensor are acquired via the two or more acquisition channels. Similarly, a sensor may be connected to two or more transmission channels, such that two transmission signals are provided concurrently to the sensor. In general, the dynamic selection switch 422 is configured to dynamically connect the sensors 410 to the acquisition channels 423 and the transmission channels 424 as desired and depending on the operating conditions of the sensors 410.

Figure 6:
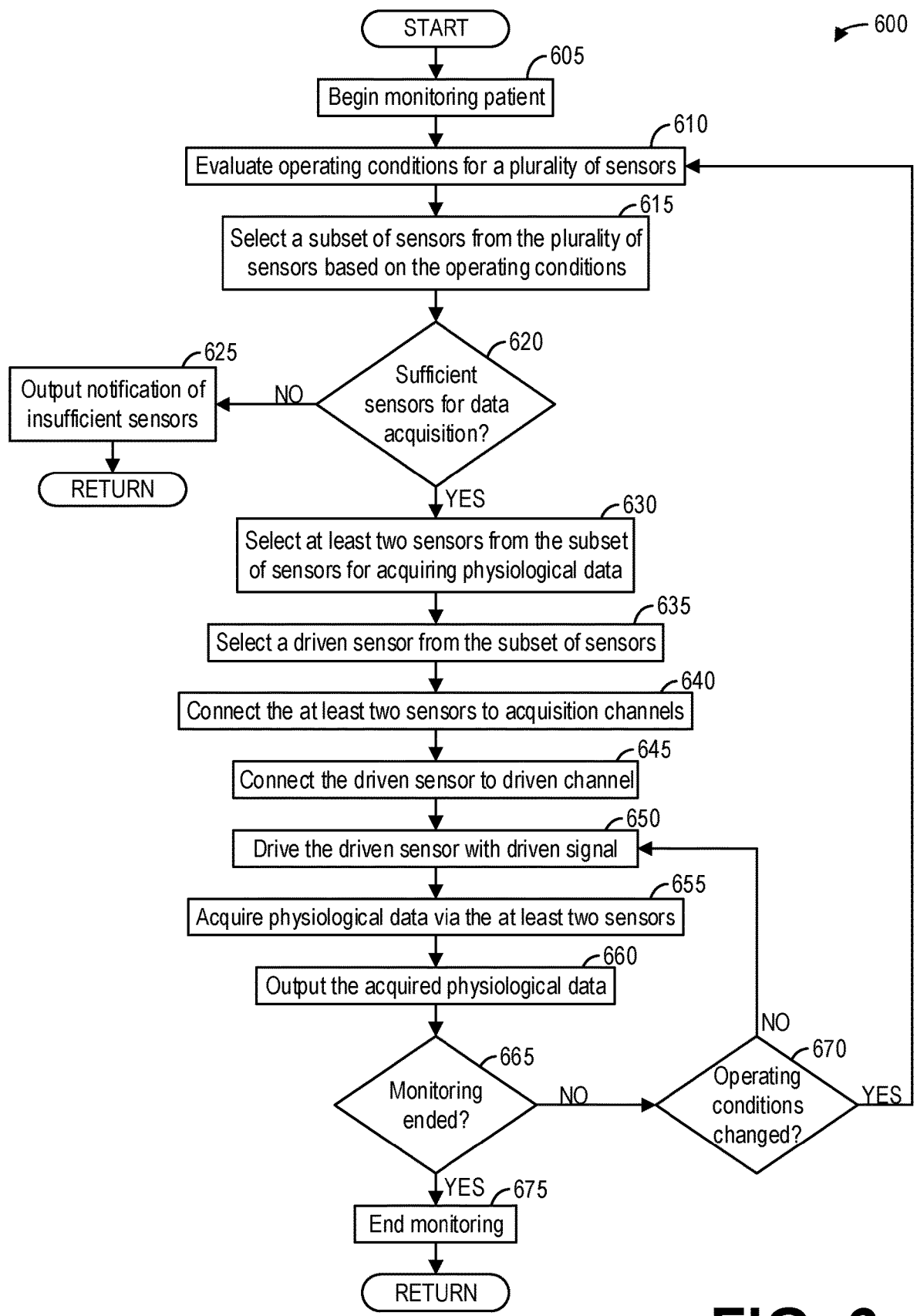
FIG. 6 shows a high-level flow chart illustrating an example method for dynamically switching sensors between acquisition and transmission channels according to an embodiment.

FIG. 6 shows a high-level flowchart illustrating an example method 600 for dynamically selecting sensors for data acquisition. In particular, method 600 relates to dynamically connecting different sensors to acquisition and transmission channels while monitoring a patient. Method 600 is described with regard to the systems and components of FIGS. 1-5, though it should be appreciated that the method 600 may be implemented with other systems and components without departing from the scope of the present disclosure. Method 600 may be implemented as executable instructions in non-transitory memory 484, for example, and may be executed by a processor 482.

Method 600 begins at 605. At 605, method 600 begins monitoring a patient. Method 600 may begin automatically monitoring the patient, for example, in response to the patient being positioned on or against a fabric cover configured with a plurality of sensors as described hereinabove. Additionally or alternatively, method 600 may begin monitoring the patient responsive to user input comprising a command to begin monitoring the patient. For example, an operator of a neonatal or infant care environment such as the neonatal or infant care environment 100 may input, via an input/output interface device 214 for example, a command to begin monitoring the patient. Further, monitoring the patient comprises continuously measuring physiological data of the patient. Monitoring the patient may further comprise evaluating the measured physiological data. Further still, monitoring the patient may comprise displaying the measured physiological data and/or the results of evaluating the measured physiological data, for example via a display such as the one or more output devices 222.

At 610, method 600 evaluates the operating conditions for a plurality of sensors. The operating conditions may include, but are not limited to, signal strength of each sensor, skin impedance for each sensor, relative position of each sensor, desired lead configuration for data acquisition, previous configuration for mapping sensors to the acquisition/transmission channels, and so on. For example, to evaluate the operating conditions of the signal strength and/or skin impedance, method 600 may evaluate the output of each sensor. The relative position of each sensor within the sensor array may be predetermined and stored in memory. Further, a desired lead configuration, such as three-lead, five-lead, or seven-lead ECG configuration, may be determined as an operating condition. Such a desired configuration may be predetermined, for example as a default configuration, or in some examples a user may select a desired lead configuration. For example, a three-lead configuration comprising two acquisition sensors and one driven sensor may comprise a default configuration, and a user may specify that a five-lead configuration is desired for the present application. Method 600 may therefore default to the default configuration in the absence of user input, but select the desired lead configuration selected by a user in the presence of user input relating to the desired lead configuration. Method 600 may further determine a previous configuration for connecting or mapping sensors to the acquisition/transmission channels when dynamically updating the selected sensors, such that method 600 may initially evaluate operating conditions of sensors neighboring previously-selected sensors when conditions change. For example, rather than evaluating the signal strength of each sensor in the plurality of sensors when the patient moves, method 600 may first evaluate the signal strength of neighboring sensors (e.g., relative to the previous configuration) to determine whether the patient has moved to the neighboring sensors.

Continuing at 615, method 600 selects a subset of sensors from the plurality of sensors based on the operating conditions. The subset of sensors may comprise each sensor of the plurality of sensors with a signal indicating direct contact of the patient with the sensor. The number of sensors in the selected subset of sensors may therefore comprise a number of sensors that is less than, equal to, or greater than a sufficient number of sensors for data acquisition. For example, at least three sensors should be in direct contact with the patient for acquiring an electrocardiogram of the patient. For other applications, a different number of sensors may be considered sufficient for data acquisition.

At 620, method 600 determines whether there are a sufficient number of sensors in the subset of sensors for data acquisition. For example, as described hereinabove, the sufficient number of sensors may comprise a minimum number of sensors for data acquisition. In some examples, the sufficient number of sensors may comprise one sensor. In examples wherein the plurality of sensors are configured to measure an electrocardiogram of the patient, the sufficient number of sensors may comprise at least three sensors for a three-lead configuration. For examples wherein a desired lead configuration is selected for monitoring the patient, the sufficient number of sensors may comprise at least a number of sensors indicated by the desired lead configuration. For example, if a three-, five-, or seven-lead configuration is selected for monitoring an electrocardiogram of the patient, then the sufficient number of sensors may comprise at least three, five, or seven sensors respectively for monitoring the patient. It should be appreciated that the number of sensors in the subset of sensors may be greater than the sufficient number of sensors, depending on the distribution of the sensors, the individual shapes of the sensors, and the positioning of the patient on or against the sensors. If there are not a sufficient number of sensors ("NO"), method 600 continues to 625. At 625, method 600 generates and outputs a notification of insufficient sensors. Method 600 then returns.

Referring again to 620, if there are a sufficient number of sensors ("YES"), method 600 proceeds to 630. At 630, method 600 selects at least two sensors from the subset of sensors for acquiring physiological data from the patient. For example, to acquire an electrocardiogram of the patient, method 600 select the at least two sensors from the subset of sensors for measuring bio-potentials of the patient. Method 600 may select two sensors from the subset of sensors for data acquisition in a three-lead configuration, four sensors from the subset of sensors for data acquisition in a five-lead configuration, six sensors from the subset of sensors for data acquisition in a six-lead configuration, and so on. Method 600 may select the at least two sensors from the subset of sensors based on the relative positions of the at least two sensors. For example, method 600 may select two sensors with a greater distance between them relative to the distance between other pairs of sensors in the subset of sensors. As an illustrative example, there are six unique pairs of sensors to select from a subset of sensors including four sensors, and method 600 may select a pair from the six unique pairs of sensors with a largest physical distance between the sensors in the pair, to improve the noise performance when measuring the electrical potential difference between the two sensors. If method 600 is selecting more than one pair of sensors from the subset of sensors, method 600 may select a number of pairs with the greatest relative distances.

Further, at 635, method 600 selects a driven sensor from the subset of sensors for driving a driven common-mode output signal to the patient. Method 600 may select the driven sensor from the subset of sensors based on the selection at 630 of the at least two sensors. For example, if the subset of sensors includes four sensors and one pair of sensors is selected at 630 for data acquisition, method 600 may select at least one sensor from the remaining two sensors in the subset of sensors as a driven sensor. The sensor selected from the remaining two sensors may be selected to provide enhanced common-mode interference reduction for the data acquisition by the pair of sensors selected for data acquisition. In some examples, the plurality of sensors includes dedicated driven sensors, as described hereinabove, and so method 600 may select the driven sensor from the dedicated driven sensors in the subset of sensors. For such examples, the absence of a dedicated driven sensor in the subset of sensors may be considered when evaluating whether there are sufficient sensors for data acquisition at 620, such that the subset of sensors may be not be considered sufficient if the subset of sensors does not include at least one sensor suitable for driving a common-mode output signal. In other examples, any sensor of the plurality of sensors may be used as a driven sensor, and so method 600 may select any suitable sensor from the remaining sensors in the subset of sensors as the driven sensor.

After selecting the at least two sensors and the driven sensor from the subset of sensors, method 600 proceeds to 640. At 640, method 600 connects the at least two sensors to acquisition channels. For example, method 600 may control the dynamic selection switch 422 to connect the at least two sensors selected for data acquisition to at least two acquisition channels. Controlling the dynamic selection switch 422 to connect the at least two sensors selected for data acquisition to the at least two acquisition channels may comprise, as an illustrative example, transmitting a control signal to the dynamic selection switch, the control signal indicating the at least two sensors and the at least two acquisition channels. The dynamic selection switch 422 may then electrically couple the at least two sensors to the at least two acquisition channels responsive to the control signal. Further, at 645, method 600 connects the driven sensor to a driven channel or transmission channel. For example, method 600 may control the dynamic selection switch 422 to connect the driven sensor to a transmission channel. Method 600 may transmit a control signal to the dynamic selection switch 422 indicating the driven sensor and the driven or transmission channel. The dynamic selection switch 422 electrically couples the driven sensor to the transmission channel responsive to the control signal.

At 650, method 600 drives the driven sensor with a driven signal. For example, method may transmit the driven signal comprising a driven common-mode output signal as described hereinabove via the transmission channel to the driven sensor. The driven signal is thus applied to the patient via the driven sensor to reduce common-mode interference. In some examples, the driven signal may be adapted based on the driven sensor, for example by adjusting the driven signal based on the position of the driven sensor relative to the at least two sensors selected for acquiring physiological data.

Meanwhile, at 655, method 600 acquires physiological data from the patient via the at least two sensors. For example, method 600 acquires, from the at least two sensors via the at least two acquisition channels, the physiological data of the patient and measured by the at least two sensors.

As the physiological data is acquired via the at least two sensors, method 600 outputs the acquired physiological data at 660. For example, method 600 may output the acquired physiological data via the one or more output devices 222. Additionally or alternatively, method 600 may output the acquired physiological data to memory, such as the one or more volatile memory devices 218 and/or the one or more non-transitory storage devices 220. Additionally or alternatively, the acquired physiological data may be output to another processing module and/or another computing device for additional processing of the acquired physiological data. The physiological data may be output as a displayed signal, for example, such as an ECG.

After outputting the acquired physiological data, method 600 continues to 665. At 665, method 600 determines whether monitoring of the patient has ended. The monitoring of the patient may end, for example, in response to user input indicating that the monitoring of the patient is complete. As another example, the monitoring of the patient may end when the patient is removed from neonatal or infant care environment 100, for example, such that the patient is not in contact with any of the sensors in the plurality of sensors.

If monitoring has not ended ("NO"), method 600 continues to 670. At 670, method 600 determines whether operating conditions have changed. Method 600 may determine that the operating conditions have changed if at least one of the signals received from the at least two sensors and/or the driven sensor indicates that the patient is not in direct contact with at least one of the sensors. For example, if a signal from a sensor indicates that the skin impedance of the sensor is below an impedance threshold, or alternatively if the signal drops below a threshold, then method 600 may determine that the operating conditions of the sensor have changed.

If operating conditions have not changed ("NO"), method 600 returns to 650 to continue driving the driven sensor and acquiring physiological data via the at least two sensors. However, if the operating conditions have changed ("YES"), method 600 returns to 610 to evaluate the operating conditions and select a new subset of sensors from the plurality of sensors based on the present operating conditions. In some examples, method 600 may evaluate each sensor of the plurality of sensors to determine which sensors are in direct contact with the patient. In other examples, method 600 may evaluate the operating conditions of the plurality of sensors, such as identifying the one or more sensors with the changed operating conditions determined at 670, and identifying one or more sensors positioned adjacent to the one or more sensors with the changed operating conditions. For example, assuming the patient has slightly shifted position with respect to the plurality of sensors such that the patient is no longer in direct contact with a sensor previously being used to acquire physiological data or drive the driven signal, method 600 may first evaluate sensors physically near or adjacent to the sensor that are not also being used to acquire physiological data and/or drive the driven signal to determine whether the patient is now in direct contact with at least one of the adjacent sensors. If none of the sensors near the sensor are in direct contact with the patient, method 600 may proceed to evaluate remaining sensors of the plurality of sensors. In this way, method 600 may identify and select a new subset of sensors from the plurality of sensors more quickly than if method 600 evaluated each sensor of the plurality of sensors during the real-time monitoring.

Method 600 thus continues to acquire physiological data of the patient via at least two sensors, dynamically selecting sensors based on real-time operating conditions, until method 600 determines at 665 that monitoring of the patient is ended ("YES"). Method 600 then proceeds from 665 to 675, wherein method 600 ends monitoring of the patient. To end monitoring of the patient, method 600 discontinues transmission of the driven signal to the driven sensor and discontinues acquisition of physiological data via the at least two sensors. Method 600 then returns.

A technical effect of the present disclosure includes the dynamic electrical connection and disconnection of sensors in a sensor array from acquisition channels and transmission channels. Another technical effect of the present disclosure includes the continuous acquisition of physiological data from a patient via different combinations of sensors in a plurality of sensors over time while monitoring the patient. Yet another technical effect of the present disclosure includes the transmission of a driven signal into a patient via different sensors in a sensor array over time in accordance with operating conditions of the different sensors while monitoring the patient.

In one embodiment, a system comprises a plurality of sensors distributed in an array and adapted to measure physiological data of a patient when in direct contact with a patient, a dynamic selection switch communicatively coupled to the plurality of sensors, a plurality of acquisition channels communicatively coupled to the dynamic selection switch, and a processor communicatively coupled to the dynamic selection switch and configured with executable instructions in non-transitory memory that when executed cause the processor to: select a subset of sensors from the plurality of sensors; control the dynamic selection switch to connect the subset of sensors to the plurality of acquisition channels; and acquire, from the subset of sensors via the plurality of acquisition channels, the physiological data of the patient.

In a first example of the system, the processor is further configured with executable instructions in the non-transitory memory that when executed cause the processor to control the dynamic selection switch to dynamically connect different subsets of sensors from the plurality of sensors to the plurality of acquisition channels while monitoring the patient. In a second example of the system optionally including the first example, to dynamically connect different subsets of sensors to the plurality of acquisition channels while monitoring the patient, the processor is further configured with executable instructions in the non-transitory memory that when executed cause the processor to: detect a loss of signal from a first sensor in the subset of sensors connected to an acquisition channel of the plurality of acquisition channels while monitoring the patient; control the dynamic selection switch to connect a second sensor of the plurality of sensors to the acquisition channel, the second sensor of the plurality of sensors positioned adjacent to the first sensor in the subset of sensors in response to detecting the loss of the signal; and acquire, from the second sensor via the acquisition channel, the physiological data of the patient. In a third example of the system optionally including one or more of the first and second examples, the processor is further configured with executable instructions in the non-transitory memory that when executed cause the processor to evaluate signal strength from each sensor of the plurality of sensors to determine which sensors are in direct contact with the patient, and select the subset of sensors from the plurality of sensors based on the evaluated signal strength of each sensor of the plurality of sensors. In a fourth example of the system optionally including one or more of the first through third examples, the system further comprises at least one transmission channel communicatively coupled to the dynamic selection switch, and the processor is further configured with executable instructions in the non-transitory memory that when executed cause the processor to: select at least one driven sensor from the subset of sensors; control the dynamic selection switch to connect the at least one driven sensor to the at least one transmission channel; and transmit, to the driven sensor via the at least one transmission channel, at least one driven signal comprising one or more of a driven common-mode output signal for reducing common-mode interference or a respiratory signal modulation signal for respiratory signal modulation. In a fifth example of the system optionally including one or more of the first through fourth examples, the system further comprises a fabric cover, wherein the plurality of sensors are distributed across and integrated into a surface of the fabric cover, and wherein the patient is positioned against the surface of the fabric cover during monitoring of the patient. In a sixth example of the system optionally including one or more of the first through fifth examples, the processor is further configured with executable instructions in the non-transitory memory that when executed cause the processor to: select two sensors from the subset of sensors with a greatest physical distance between the two sensors relative to relative distances of other sensor pairings in the subset of sensors; control the dynamic selection switch to connect the two sensors to the plurality of acquisition channels; and acquire, from the two sensors via the plurality of acquisition channels, the physiological data of the patient. In a seventh example of the system optionally including one or more of the first through sixth examples, the processor is further configured with executable instructions in the non-transitory memory that when executed cause the processor to generate and output a notification of an insufficient number of sensors responsive to the subset of sensors comprising fewer than a threshold number of sensors. In an eighth example of the system optionally including one or more of the first through seventh examples, each sensor of the plurality of sensors comprises a lead for acquiring an electrocardiogram, and wherein the physiological data comprises the electrocardiogram.

In another embodiment, an apparatus comprises a dynamic selection switch communicatively coupled to a plurality of sensors and a plurality of acquisition channels, the dynamic selection switch configured to dynamically connect a subset of sensors of the plurality of sensors to the plurality of acquisition channels for acquiring physiological data via the sensors.

In a first example of the apparatus, the dynamic selection switch is further communicatively coupled to a transmission channel, and the dynamic selection switch is configured to dynamically connect a sensor of the plurality of sensors to the transmission channel for transmitting a driven signal via the transmission channel to the sensor. In a second example of the apparatus optionally including the first example, the dynamic selection switch is communicatively coupled to a processor, wherein the dynamic selection switch dynamically connects the subset of sensors to the plurality of acquisition channels responsive to receiving a command from the processor indicating the subset of sensors of the plurality of sensors. In a third example of the apparatus optionally including one or more of the first and second examples, the plurality of sensors are spaced apart in a sensor array, and the dynamic selection switch is further configured to, in response to a skin impedance measured by a sensor of the subset of sensors connected to an acquisition channel of the plurality of acquisition channels dropping below a threshold impedance, automatically connect an adjacent sensor of the plurality of sensors to the acquisition channel, the adjacent sensor positioned adjacent to the sensor of the subset of sensors in the sensor array. In a fourth example of the apparatus optionally including one or more of the first through third examples, the dynamic selection switch comprises a MOSFET-based switch. In a fifth example of the apparatus optionally including one or more of the first through fourth examples, the dynamic selection switch connects a sensor of the plurality of sensors to at least one acquisition channel of the plurality of acquisition channels. For example, the sensor may be simultaneously connected to one or more acquisition channels.

In yet another embodiment, a method comprises selecting a subset of sensors from a plurality of sensors, the plurality of sensors integrated into a fabric cover and adapted to measure physiological data of a patient when in direct contact with a patient, controlling a dynamic selection switch to connect the subset of sensors to a plurality of acquisition channels, and acquiring, from the subset of sensors via the plurality of acquisition channels, the physiological data of the patient.

In a first example of the method, the method further comprises evaluating operating conditions for each sensor of the plurality of sensors to determine which sensors of the plurality of sensors are in direct contact with the patient, wherein the subset of sensors comprise the sensors in direct contact with the patient. In a second example of the method optionally including the first example, the method further comprises selecting the subset of sensors from the plurality of sensors based on relative positions of each sensor of the plurality of sensors. In a third example of the method optionally including one or more of the first and second examples, the method further comprises selecting a new subset of sensors from the plurality of sensors responsive to detecting loss of signal from at least one sensor of the subset of sensors, and controlling the dynamic selection switch to connect the new subset of sensors to the plurality of acquisition channels. In a fourth example of the method optionally including one or more of the first through third examples, the method further comprises selecting a driven sensor from the plurality of sensors, controlling the dynamic selection switch to connect the driven sensor to a transmission channel, and transmitting, to the driven sensor via the transmission channel, a driven common-mode output signal to reduce common-mode interference. In a fifth example of the method optionally including one or more of the first through fourth examples, the method further comprises selecting a new driven sensor from the plurality of sensors responsive to operating conditions of the driven sensor indicating that the driven sensor is not in direct contact with the patient, controlling the dynamic selection switch to connect the new driven sensor to the transmission channel, and transmitting, to the new driven sensor via the transmission channel, the driven common-mode output signal.

FIGS. 1-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
    a plurality of sensors distributed in an array and adapted to measure physiological data of a patient when in direct contact with the patient;
    a fabric cover having a surface configured to have the patient placed thereon, wherein the plurality of sensors are distributed across and integrated into the surface of the fabric cover, and wherein the surface of the fabric cover is sized such that the patient is smaller than the fabric cover and the patient is repositionable on the surface of the fabric cover;
    a dynamic selection switch communicatively coupled to the plurality of sensors;
    a plurality of acquisition channels communicatively coupled to the dynamic selection switch;
    a processor communicatively coupled to the dynamic selection switch and configured with executable instructions in non-transitory memory that when executed cause the processor to:
        select a subset of sensors from the plurality of sensors;
        control the dynamic selection switch to connect the subset of sensors to the plurality of acquisition channels by: disconnecting the plurality of acquisition channels from any of the subset of sensors that are connected and are determined to not be in direct contact with the patient; then connecting each of the subset of sensors with one of the plurality of acquisition channels; and then determining if each of said connected subset of sensors is in direct contact with the patient; and
        acquire, from the subset of sensors via the plurality of acquisition channels, the physiological data of the patient.

2. The system of claim 1, wherein the processor is further configured with executable instructions in the non-transitory memory that when executed cause the processor to control the dynamic selection switch to dynamically connect different subsets of sensors from the plurality of sensors to the plurality of acquisition channels while monitoring the patient.

3. The system of claim 2, wherein, to dynamically connect different subsets of sensors to the plurality of acquisition channels while monitoring the patient, the processor is further configured with executable instructions in the non-transitory memory that when executed cause the processor to:
    detect a loss of signal from a first sensor in the subset of sensors connected to an acquisition channel of the plurality of acquisition channels while monitoring the patient;
    control the dynamic selection switch to connect a second sensor of the plurality of sensors to the acquisition channel, the second sensor of the plurality of sensors positioned adjacent to the first sensor in the subset of sensors in response to detecting the loss of the signal; and
    acquire, from the second sensor via the acquisition channel, the physiological data of the patient.

4. The system of claim 1, wherein the processor is further configured with executable instructions in the non-transitory memory that when executed cause the processor to evaluate signal strength from each sensor of the plurality of sensors to determine which sensors are in direct contact with the patient, and select the subset of sensors from the plurality of sensors based on the evaluated signal strength of each sensor of the plurality of sensors.

5. The system of claim 1, further comprising at least one transmission channel communicatively coupled to the dynamic selection switch, wherein the processor is further configured with executable instructions in the non-transitory memory that when executed cause the processor to:
select at least one driven sensor from the subset of sensors;
control the dynamic selection switch to connect the at least one driven sensor to the at least one transmission channel; and
transmit, to the at least one driven sensor via the at least one transmission channel, at least one driven signal comprising one or more of a driven common-mode output signal for reducing common-mode interference or a respiratory signal modulation signal for respiratory signal modulation.

6. The system of claim 1, wherein the patient is positioned against the surface of the fabric cover during monitoring of the patient, wherein the patient is positioned on top of a platform or mattress and the fabric cover is in the form of a platform or mattress cover, and wherein the plurality of sensors and the dynamic selection switch are configured so as to measure physiological data of the patient as the patient moves around on the surface of the fabric cover.

7. The system of claim 1, wherein the processor is further configured with executable instructions in the non-transitory memory that when executed cause the processor to:
select two sensors from the subset of sensors with a greatest physical distance between the two sensors relative to relative distances of other sensor pairings in the subset of sensors;
control the dynamic selection switch to connect the two sensors to the plurality of acquisition channels; and
acquire, from the two sensors via the plurality of acquisition channels, the physiological data of the patient.

8. The system of claim 1, wherein the processor is further configured with executable instructions in the non-transitory memory that when executed cause the processor to generate and output a notification of an insufficient number of sensors responsive to the subset of sensors comprising fewer than a threshold number of sensors.

9. The system of claim 1, wherein each sensor of the plurality of sensors comprises a lead for acquiring an electrocardiogram, and wherein the physiological data comprises the electrocardiogram.

10. The system of claim 1, wherein the processor is further configured with executable instructions in the non-transitory memory that when executed cause the processor to determine whether any of the subset of sensors are in direct contact with the patient based on a measured skin impedance of the patient.

11. An apparatus, comprising:
a dynamic selection switch communicatively coupled to a plurality of sensors and a plurality of acquisition channels, the dynamic selection switch configured to dynamically disconnect the plurality of acquisition channels from any of a subset of sensors of the plurality of sensors that are connected and are determined to not be in direct contact with a patient, then connect each of the subset of sensors with one of the plurality of acquisition channels, then determine if each of said connected subset of sensors is in direct contact with the patient, and then acquire physiological data of the patient via the sensors; and
a fabric cover having a surface configured to have the patient placed thereon, wherein the plurality of sensors are distributed across and integrated into the surface of the fabric cover, and wherein the surface of the fabric cover is sized such that the patient is smaller than the fabric cover and the patient is repositionable on the surface of the fabric cover.

12. The apparatus of claim 11, wherein the dynamic selection switch is further communicatively coupled to a transmission channel, and wherein the dynamic selection switch is configured to dynamically connect a sensor of the plurality of sensors to the transmission channel for transmitting a driven signal via the transmission channel to the sensor.

13. The apparatus of claim 11, wherein the dynamic selection switch is communicatively coupled to a processor, wherein the dynamic selection switch dynamically connects the subset of sensors to the plurality of acquisition channels responsive to receiving a command from the processor indicating the subset of sensors of the plurality of sensors.

14. The apparatus of claim 11, wherein the plurality of sensors are spaced apart in a sensor array, and wherein the dynamic selection switch is further configured to, in response to a skin impedance measured by a sensor of the subset of sensors connected to an acquisition channel of the plurality of acquisition channels dropping below a threshold impedance, automatically connect an adjacent sensor of the plurality of sensors to the acquisition channel, the adjacent sensor positioned adjacent to the sensor of the subset of sensors in the sensor array.

15. The apparatus of claim 11, wherein the dynamic selection switch connects a sensor of the plurality of sensors to at least one acquisition channel of the plurality of acquisition channels, wherein the patient is positioned on top of a platform or mattress and the fabric cover is in the form of a platform or mattress cover, and wherein the plurality of sensors and the dynamic selection switch are configured so as to measure physiological data of the patient as the patient moves around on the surface of the fabric cover.

16. A method, comprising:
selecting a subset of sensors from a plurality of sensors, the plurality of sensors integrated into a fabric cover and adapted to measure physiological data of a patient when in direct contact with a patient, the fabric cover having a surface configured to have the patient placed thereon, wherein the plurality of sensors are distributed across and integrated into the surface of the fabric cover, and wherein the surface of the fabric cover is sized such that the patient is smaller than the fabric cover and the patient is repositionable on the surface of the fabric cover;
controlling a dynamic selection switch to disconnect a plurality of acquisition channels from any of the subset of sensors that are connected and are determined to not be in direct contact with the patient, then connect each of the subset of sensors with one of the plurality of acquisition channels, and then determine if each of said connected subset of sensors is in direct contact with the patient; and
acquiring, from the subset of sensors via the plurality of acquisition channels, the physiological data of the patient.

17. The method of claim 16, further comprising evaluating operating conditions for each sensor of the plurality of sensors to determine which sensors of the plurality of sensors are in direct contact with the patient, wherein the subset of sensors comprise the sensors in direct contact with the patient.

18. The method of claim 17, further comprising selecting the subset of sensors from the plurality of sensors based on relative positions of each sensor of the plurality of sensors.

19. The method of claim 16, further comprising selecting a new subset of sensors from the plurality of sensors responsive to detecting loss of signal from at least one sensor of the subset of sensors, and controlling the dynamic selection switch to connect the new subset of sensors to the plurality of acquisition channels, wherein the patient is positioned on top of a platform or mattress and the fabric cover is in the form of a platform or mattress cover, and wherein the plurality of sensors and the dynamic selection switch are configured so as to measure physiological data of the patient as the patient moves around on the surface of the fabric cover.

20. The method of claim 16, further comprising selecting a driven sensor from the plurality of sensors, controlling the dynamic selection switch to connect the driven sensor to a transmission channel, and transmitting, to the driven sensor via the transmission channel, a driven common-mode output signal to reduce common-mode interference.

21. The method of claim 20, further comprising selecting a new driven sensor from the plurality of sensors responsive to operating conditions of the driven sensor indicating that the driven sensor is not in direct contact with the patient, controlling the dynamic selection switch to connect the new driven sensor to the transmission channel, and transmitting, to the new driven sensor via the transmission channel, the driven common-mode output signal.

\* \* \* \* \*